United States Patent
Hurtmanns et al.

(10) Patent No.: US 9,426,981 B2
(45) Date of Patent: Aug. 30, 2016

(54) ANTIMICROBIAL COMPOSITION HAVING SKINCARE PROPERTIES

(76) Inventors: Stephan Hurtmanns, Hamburg (DE); Sven Eggerstedt, Hamburg (DE)

( * ) Notice: Subject to any disclaimer, the term of this patent is extended or adjusted under 35 U.S.C. 154(b) by 0 days.

(21) Appl. No.: 13/996,744

(22) PCT Filed: Dec. 16, 2011

(86) PCT No.: PCT/EP2011/006382
§ 371 (c)(1), (2), (4) Date: Jun. 21, 2013

(87) PCT Pub. No.: WO2012/084164
PCT Pub. Date: Jun. 28, 2012

(65) Prior Publication Data
US 2013/0274345 A1 Oct. 17, 2013

(30) Foreign Application Priority Data
Dec. 22, 2010 (DE) .................. 10 2010 055 528

(51) Int. Cl.
| | | |
|---|---|---|
| *A01N 25/34* | (2006.01) |
| *A01N 25/00* | (2006.01) |
| *A01N 25/30* | (2006.01) |
| *A01N 31/02* | (2006.01) |
| *A61K 8/31* | (2006.01) |
| *A61K 8/34* | (2006.01) |
| *A61K 8/37* | (2006.01) |
| *A61K 8/81* | (2006.01) |
| *A61K 8/893* | (2006.01) |
| *A61K 31/045* | (2006.01) |
| *A61Q 17/00* | (2006.01) |
| *A61Q 19/00* | (2006.01) |
| *A61Q 19/10* | (2006.01) |
| *D06M 16/00* | (2006.01) |

(52) U.S. Cl.
CPC .............. *A01N 25/00* (2013.01); *A01N 25/30* (2013.01); *A01N 31/02* (2013.01); *A61K 8/31* (2013.01); *A61K 8/34* (2013.01); *A61K 8/37* (2013.01); *A61K 8/8152* (2013.01); *A61K 8/893* (2013.01); *A61K 31/045* (2013.01); *A61Q 17/005* (2013.01); *A61Q 19/00* (2013.01); *A61Q 19/10* (2013.01); *D06M 16/00* (2013.01)

(58) Field of Classification Search
None
See application file for complete search history.

(56) References Cited

U.S. PATENT DOCUMENTS

| | | |
|---|---|---|
| 2004/0102429 A1 | 5/2004 | Modak |
| 2005/0142079 A1* | 6/2005 | Garrison et al. ............... 424/59 |
| 2007/0071705 A1 | 3/2007 | De Oliveira |

FOREIGN PATENT DOCUMENTS

| | | |
|---|---|---|
| EP | 0 689 767 | 1/1996 |
| EP | 1 281 319 | 2/2003 |
| EP | 1 374 847 | 1/2004 |
| EP | 0 930 065 | 9/2004 |
| WO | WO 2006/096239 | 9/2006 |
| WO | WO 2006096239 A1 * | 9/2006 |
| WO | WO 2008/034244 | 3/2008 |
| WO | WO 2009/052566 | 4/2009 |

OTHER PUBLICATIONS

International Search Report, dated Jun. 12, 2012, issued in PCT application PCT/EP2011/006382, 2 pages.
International Preliminary Report on Patentability, dated Jun. 25, 2013, issued in PCT application PCT/EP2011/006382, 9 pages.
Manusept Basic—Hygienic and Surgical Hand Disinfection, Mar. 1, 2008. pp. 1-2, URL: http://www.bode-chemie.com/products/hands/product_information/manusept_basic_int.pdf.
Gels for Dermal Application, by Rolf Daniels, Pharmazeutische Zeitung online, vol. 43/2002 (2002), http://pharmazeutische-zeitung.de/index.php?id=titel_43_2002.

* cited by examiner

*Primary Examiner* — Susan Tran
(74) *Attorney, Agent, or Firm* — Nash and Titus, LLC

(57) ABSTRACT

The invention relates to an antimicrobial composition which contains 80-95% by weight of ethanol 1-propanol, 2-propanol or the fixtures thereof. The hydroalcoholic composition according to the invention is preferably used in hand disinfectants. Due to the oil components contained therein it is skin-friendly and has good skin care properties, thus making it possible to combine good disinfectant properties with good use properties and skin-friendliness.

11 Claims, No Drawings

ANTIMICROBIAL COMPOSITION HAVING SKINCARE PROPERTIES

This application claims priority from PCT/EP2011/006382 (WO 2012/084104), filed Dec. 11, 2011, and from German application DE 10 2010 055 528.2, filed Dec. 16, 2010, and the entire contents of these applications are incorporated herein by reference.

BACKGROUND OF THE INVENTION

The present invention relates to an antimicrobial composition for the disinfection of hands, based on 80-90 wt % ethanol, 1-propanol, 2-propanol or their mixtures, that has skincare properties that are imparted visually by the appearance of the composition.

For the disinfection of hands, in particular for the hygienic disinfection of hands, alcoholic solutions are preferably used. These preparations with a high alcohol concentration have a broad effectiveness spectrum against bacteria, molds and various viruses. As in particular in the case of medical personnel, e.g., in clinics, a frequent disinfection takes place, the disinfectant used must have, in addition to a sufficient disinfection effect, also a good skin-friendliness. Therefore, auxiliary care substances are usually added to the disinfectants.

EP-0930065-B1 describes an antimicrobial compound with a lotion-like appearance based on a mixture of 40-80% by volume C2- and/or C3 alcohol and water, acrylic polymer thickeners, antimicrobial cationic compounds and softeners and silicone-based waxes and oils as main care component. In the case of rather high alcohol concentrations the compounds display, in particular in the absence of a sufficient amount of water, a low stability as well as the formation of rather small particles when the compound is rubbed on the skin.

EP-1374847-A1 describes antimicrobial hand lotions in which the liquid phase is formed with a ratio of alcohol to water of 35-65 wt % to 100-0 wt %. With a mixture of at least two emulsifies a viscosity of at least 4,000 cps, preferably 80,000 to 500,000 cps is adjusted, whereby the compound contains no thickener. In order to improve the moisture content of the skin softeners are added.

WO-2006/096239-A1 discloses antimicrobial emulsions with 50-95 wt % C2 to C4 alcohol, or 62-75 wt % C2 to C4 alcohol and/or ethanol cross-linked acrylate thickeners and skincare components, whereby the latter can be selected from a plurality of commercial skincare components and silicone-free emulsifiers.

US 2004/0102429A1 describes a composition that should be effective against skin irritations and can be used in combination with alcohol-based disinfectants, whereby the composition contains at least two organic zinc salts. In addition, gel producers, thickeners, care substances, silicone oils, etc. can be used.

The known compositions contain silicone oils as main care substances. Classic surface-active agent systems are required in order to stabilize the formulations or in order to achieve a thickening of the entire recipe. The skin feeling during usage is not in the foreground with these compositions.

In the publication with the title "Gele für die dermale Applikation" of the author Rolf Daniels (Pharmazeutische Zeitung, online edition 43/2002, http://www.pharmazeutische-zeitung.de/index/php?id=titel_43_2002, last sought on Dec. 15, 2010), emulsion-like systems are described that consist of a hydrophilic continuous phase and a lipophilic disperse phase. The disperse phase is not stabilized by classic emulsifiers but rather by macromolecules. The physical stability of these hydrodispersion gels is achieved by a fine distribution of the lipids and by the flow boundary of the outer phase.

Furthermore, disinfection agents are known in the market that have an alcohol content of <80 wt % but are not an emulsion but rather clean, transparent gels. Furthermore, emulsions are known that have an alcohol content of about 60 wt % and contain other antimicrobial active substances and there are those that contain an emulsifier-thickener combination and care substances with an alcohol content of about 60 wt %.

It turned out that the compliance, that is, the observing of regulations, of hygienic hand disinfection is only about 50%. This is frequently due to a poor skin feeling when using alcohol products. It has therefore been the goat of tire producers for some time to make products available that have a good skin-friendliness. To this end even gels and lotions, among others, are being brought to the market. The disadvantage of the thickeners used in these compositions is that the product is frequently perceived as sticky on the skin, which for its part leads to a lesser readiness to use the product. In addition, in some instances wear can occur on the skin, that is also described as "balling". The stickiness as well as the balling are perceived in particular as unpleasant if one is working with protective gloves since this makes it difficult to put them on and off. In addition, working with bandage material or preparing or administering drugs is made quite difficult with sticky hands. To the extent that a lesser amount of thickener is used, many of the products are not sufficiently stable as soon as they have a high alcohol content. However, the high alcohol component is not necessary for a sufficient disinfection.

Therefore, starting from this state of the art there is the problem that there are no stable compositions with antimicrobial effectiveness according to DIN EN 1500 with pleasant properties of use and good care properties at the same time for improving the compliance with the hygienic disinfection of hands.

SUMMARY OF THE INVENTION

The present invention addresses the problem described above with a skincare disinfectant that has a high antimicrobial effectiveness according to DIN EN 1500 with pleasant properties of use such as, e.g., no stickiness of the product, no formation of wear on the skin, that can be readily distributed, has a good absorption capacity and a high effectiveness of care.

The problem is solved in accordance with the invention by an antimicrobial composition containing a) 80-95 wt % ethanol t-propanol, 2-propanol or their mixtures, b) one or more silicone-containing emulsifiers, c) one or more thickeners based on cross-linked polyacrylic acid or its derivatives, d) at least two silicone-free oil components selected from unsaturated or saturated, linear or branched aliphatic hydrocarbons, fatty alcohols, fatty acid esters and their mixtures, whereby the oil components are selected from the groups comprising i) rapid spread behavior, ii) average spread behavior and iii) slow spread behavior, whereby at least two oil components are selected from different groups i)-iii), e) water.

This composition combines the advantages of a care lotion and the properties of use of a hand disinfectant. The disadvantages of the instability and of the particle formation during rubbing indicated in EP 0 930 065B1 were surprisingly able to be overcome.

The antimicrobial compound preferably contains at least one other component, selected from f) pH regulators,
g) opacifiers,
h) other antimicrobial active substances and
j) co-thickeners.

Other embodiments and subject mater are described below.

DETAILED DESCRIPTION OF THE PREFERRED EMBODIMENTS

The antimicrobial compound in accordance with the invention preferably contains 83-89 wt %, especially preferably 85-87 wt % ethanol, 1-propanol, 2-propanol or their mixtures. The silicone-containing emulsifier b) is preferably a silicone-containing, non-ionic emulsifier or in the case of several silicone-containing emulsifiers preferably at least one is a silicone-containing, non-ionic emulsifier.

Emulsifiers are compounds with a lipophilic (that is, oil-soluble) component and with a hydrophilic (water-soluble) component permanently chemically connected to it. These compounds settle on the boundary surface between aqueous and oily compounds and therefore make the formation of an emulsion possible. The emulsifiers used are silicone-containing emulsifiers whose lipophilic part is formed, for example, from a dimethicone (polydimethylsiloxane), while the hydrophilic part is formed, for example, from water-soluble polyethylene glycol (PEG) and/or polypropylene glycol (PPG).

The emulsifier and/or emulsifiers b) is/are contained in amount of 0.1-4.0 wt %, preferably 0.1-2.0 wt %, especially preferably 0.1-0.9 wt %, quite especially preferably 0.2-0.7% in the composition. The silicone-based, non-ionic emulsifier is preferably selected from copolymers of dimethicone with PEG and/or PPG with the same or different chain lengths, preferably selected further from cetyl PEG/PPG-10/1-dimethicone, bis-PEG/PPG-20/5 PEG/PPG-20/5-dimethicone, methoxy PEG/PPG-25/4-dimethicone and/or dimethicone, further preferably 0.1-0.9 wt %-bis-PEG/PPG-20/5-dimethicone, methoxy PEG/PPG-25/4-dimethicone. The antimicrobial composition of the invention preferably contains no other cationic or anionic or amphoteric emulsifiers.

The antimicrobial composition preferably contains 0.01-0.5 wt %, especially preferably 0.1-0.3 wt %, quite especially preferably 0.15-0.27% of at least one thickener c) on the basis of cross-linked polyacrylic acid or its derivatives. The acrylic acid polymers are also designated as carbomers. They are high-molecular compounds and are customarily used in the pharmaceutical or cosmetic industry for the thickening but also for dispersion and emulsion formation of topical preparations. The thickener is preferably acrylate/$C_{10-30}$ alkyl acrylate cross polymer (INCI). A suitable thickener is, for example, Carbopol® EDT 2020 NF or Carbopol® Ultrez 10 NF from the Lubrizol company.

The thickening power or the viscosity of the preparation is preferably adjusted via the amount of the added co-thickener j), preferably selected from the group of amines, preferably selected from N,N,N',N'-tetrakis-(hydroxyalkyl)-ethylene diamine, whereby the hydroxyalkyl group is preferably 2-hydroxy propyl. The co-thickener is preferably contained in the compound of the invention in an amount of 0-1.0 wt %, especially preferably 0.01-1.0 wt %, more preferably 0.2-0.6 wt %, quite especially preferably 0.3-0.54. The weight ratio of thickener c) to co-thickener j) is preferably 1:1.5 to 1:2.5, preferably 1:2.

The pH regulator or regulators f) selected from citric acid, lactic acid, tartaric acid, pyroglutamic acid, ascorbic acid, potassium hydroxide- and/or sodium hydroxide is/are preferred.

The antimicrobial compound preferably contains as opacifier g) non-soluble substances that result in a whitish-opaque appearance such as, for example, powdery polyamide particles (for example, Orgasol® Caresse of the Arkema Inc. company; INCI: polyamide-5) or waxy particles in the form of mixtures of glycol distearate, cocoamidopropylbetain, cocoamidomonoethanolamine, sodium laureth sulfate and/or PEG-laurylether (for example, Euperlan® PK 771, PK 810, PK 900, PK 3000, PK 4000 or PK4500 of the Cognis Corp.).

The antimicrobial compound of the invention contains at least two oil components, preferably the antimicrobial compound of the invention contains at least 3 oil components, more preferably at least four oil components, more preferably at least 5 oil components, whereby the oil components are selected from the groups comprising:

i) rapid spread behavior (highly spreading oils),
ii) average spread behavior (average spreading oils,
iii) slow spread behavior (low spreading oils), whereby two or more oil components are selected from different groups i) to iii).

Spread behavior denotes the ability of a substance to spread out on a solid body. A drop that strikes the skin surface moistens the surface as a function of its surface tension and of its viscosity. A substance with a high surface tension moistens only a small surface on account of the semispherical shape conditioned by this and therefore has a poor spread behavior. A substance with a slight surface tension and a low viscosity moistens a large skin surface since it spreads out more rapidly on the surface. This substance accordingly has a rapid spread behavior and is highly spreading. A distinction is made between low spreading, average spreading and highly spreading oils. Low spreading oils have a spread behavior of below 450 $mm^2$/10 minutes, average spreading oils have a spread behavior from 450-1000 $mm^2$/10 minutes and highly spreading oils have a spread behavior from above 1000 $mm^2$/10 minutes. The spread value is determined with the aid of an extensometer. Here, a substance sample with a certain volume is placed centered between two glass plates and tire upper plate loaded at defined intervals with weighing pieces in accordance with Voigt (R. Voigt, Pharmazeutische Technologie—Für Studium und Beruf, Wissenschaftliche Verlagsgesellschaft mbH Stuttgart, $9^{th}$ edition, 2000, pp. 333-334). The spreading-out surfaces resulting with increasing load constitute a characteristic for the spreadability. The classification of the above-cited spread values can take place, for example, according to Raab, Kindl (W. Raab, U. Kindl, Pflegekosmetik—Ein Leitfaden, Wissenschaftliche Verlagsgesellschaft mbH Stuttgart, $4^{th}$ edition, 4004, pp. 204-205).

Highly spreading oil components are, for example, isopropyl myristate, isopropyl palmitate, cetarylethylhexanoate. Oil components with average spread behavior are, for example, ethylhexylpalmitate, ethylhexylstearate, heptamethylnonane, capryl-/caprin-triglyceride. Oil components with slow spread behavior suitable in accordance with the invention are, for example, Paraffinum subliquidum, octyldodecanol, isocetylpalmitate.

Furthermore, the spread properties are a function of the chain length of the oil components used. The slowly spreading oils usually have a longer carbon chain and a higher polarity then the rapidly spreading oils. It turned out that the skin feeling and the application properties can be significantly improved by working in oil components with a different spread behavior. A positive skin feeling results at the beginning of the application by the rapidly spreading oils whereas a pleasant skin feeling is retained during the use of the average and/or slowly spreading oils even after the application, which achieves an improved rubbing-in behavior without transition. If the oil components are selected in such a manner that a spreading graduation is comprised over the range from high to low regarding the chain length and/or the spreading behavior, the effect can be adjusted and improved. Thus, au "oil cascade" is preferably used, whereby at least two oil components, preferably at least 5 oil components with different spreading behaviors are used, which forms an oil cascade. In order that a pleasant care feeling is achieved, preferably 50% of the total amount of the oil components used should have a slow spreading behavior.

The antimicrobial composition furthermore contains at least 1.5 wt % soluble oil components and at the same time insoluble oil components of at the most 4.0 wt %, whereby the total amount of soluble and insoluble oil components in the antimicrobial composition is at the most 6.0 wt %. The antimicrobial composition of the invention, preferably contains at least 1.5 wt % Paraffinum subliquidum, isopropylpalmitate or their mixtures and cetarylethylhexanoate myristyl alcohol, heptamethylnonane or their mixtures at at the most 4.0 wt %, whereby the total amount of soluble and insoluble oil components in the antimicrobial composition is at the most 6.0 wt %.

It turned out that an opacity of the solution is achieved by the use of oil components that are insoluble in the alcohol components. The opacity of the solution results in a whitish or while product. The caring property of the product is optically supported by this appearance. Since the color white is frequently understood as a symbol of purity in Western culture, the properties "cleaning" and "caring" tend to be associated with white products. Therefore, the positive shin care properties are emphasized by the color. This should result in an improvement of the compliance with hand disinfection. The use of silicone oils such as, e.g., polydimethylsiloxane (dimethicone) or decamethylcyclopentasiloxane (cyclomethicone) does not support the optical appearance of the emulsions in accordance with the invention since the cited silicone oils are clear, transparent oily liquids that are soluble in alcohols.

The obtention of a stable, opaque composition surprisingly succeeded, although it was to be expected that given an alcohol content of 80% and more the oil components would be present in a clear solution.

The antimicrobial composition in accordance with the invention is preferably present as an emulsion, lotion, gel or hydrodispersion gel.

Furthermore, the antimicrobial composition in accordance with the invention can contain, in addition to the monovalent $C_2/C_3$ alcohols, other antimicrobial active substances/remanance active substances h), whereby they are preferably contained in an amount of 0-5.0 wt %. Suitable antimicrobial active substances are preferably selected from the group of anionic and non-ionic active substances, preferably from diols or phenoxyethanol.

In a preferred embodiment the antimicrobial composition of the invention consists of a) 80-95 wt % ethanol, 1-propanol, 2-propanol or their mixtures, b) 0.1-4.0 wt % of one or more silicone-containing emulsifiers, c) 0.01-0.5 wt % of one or more thickeners based on cross-linked polyacrylic acid and its derivatives, d) 1.5-6.0 wt % of at least two silicone-free oil components selected from skincare hydrocarbons, fatty alcohols, fatty acid esters and their mixtures, whereby the oil components are selected from the groups comprising i) rapid spread behavior, ii) average spread behavior and in) slow spread behavior, whereby at least two oil components are selected from different groups i)-iii), e) 4-18 wt % water, j) 0.01-1.0 wt %, preferably 0.2-0.6 wt % co-thickener, selected from N,N,N',N'-tetrakis-(hydroxyalkyl)-ethylene diamine, whereby the hydroxyalkyl group is preferably 2-hydroxypropyl, whereby the weight ratio c): j) is preferably 1:1.5 to 1:2.5 and preferably 1.2.

The antimicrobial composition in accordance with the invention preferably has a dynamic viscosity of 1 to 12 Pa*s, or 1 to 5 Pa*s, measured at 20° C. (+/−0.5° C.) with a Brookfield rotation viscosimeter model DV-II+, spindle sizes 2, 3, 4 or 5 at 10 rpm. The viscosity can be appropriately adjusted by the charging of the thickener. The viscosity is preferably adjusted in such a manner mat the antimicrobial composition of the invention can be readily applied on the surface to be disinfected and has a pleasant rubbing-in behavior.

The opacity perceived as white color preferably results from an opacity value of at least 200 NTU, preferably at least 500 NTU, especially preferably at least 800 NTU. Tire determination of the opacity of the antimicrobial compositions of the invention took place according to on optical method described in the European Drug Book (2.2.1 Ph. Eur., $6^{th}$ edition, basic work 2008). This concerned a test compared to a series of reference samples with a defined degree of opacity by a 90° measuring of scattered light. The reference samples consisted of a dispersion of formazine (a reaction product consisting of hexamethylene and hydrazinium sulfate) in Aqua purificata. The unit NTU (Nephelometric Turbidity Unit) corresponds here to the German unit TE/F (Cupidity Unit Formazine). The determination of opacity is a relative measuring method since the opacity does not represent any physical magnitude. The hand disinfectant in accordance with the invention has a phi in the range of 6-9, preferably 7-9, especially preferably 8-9. Unless otherwise described, the wt % indications refer to the weight of the total composition.

The antimicrobial composition in accordance with the invention is used as a disinfectant, in particular for the disinfection of animated surfaces, especially surfaces containing microorganisms (e.g., unbroken skin, broken skin, wounds, mucous membranes, etc.)—and in particular for the disinfection of hands, especially preferably for the hygienic and surgical disinfection of hands. In order to check the effectiveness, the antimicrobial composition in accordance with the invention was subjected to an examination according to DIN EN 1500 (October, 1997). DIN EN 1500 specifics a test method that simulates the practical use of a product for the hygienic disinfection of hands. It determines by the reduction of the transient skin flora on the artificially contaminated hands of volunteer test subjects whether the test product meets the requirements. The hygienic disinfection of hands is defined here as "treatment of the hands after a contamination by rubbing in (without the addition of water) with a bactericide product against transient microorganisms in order to prevent their transmission; the resident skin flora is not taken into consideration here," The reduction is expressed here with the aid of the so-called reduction factor (RF). The RF is the difference from the decadal logarithm of the number of colony-binding units (KBE) before and after the treatment:

log RF=log pre value (*KBE*)−log post value (*KBE*).

The achieved average reduction of the test germs must not be significantly lower man the reduction achieved by a reference disinfection of hands with 60% by volume 2-propanol.

Performance:

The hands of at least 12 test subjects are washed for one minute with potash soap and subsequently dried off with paper hand towels. The hands are then held up to the middle of the hand for 5 seconds in the contamination liquid with *E. coli* bacteria (strain K 12, NCTC 10538). Then the hands are dried in air for 3 minutes and immediately thereafter the fingertips including the thumb are thoroughly kneaded for one minute in a Petri dish per hand with 10 ml of a nutrient medium (trypton-soybean solution, TSL) (pre value). Immediately following and without further contamination the hand disinfection is carried out, either with the reference alcohol or with the test product (rub reference alcohol: 2 times 3 ml for 30 seconds each according to the standard rubbing-in method. DIN EN 1500, supplement A, test product: according to the instructions of the manufacturer, here: 3 ml for 30 seconds). After the disinfection the fingers are washed off for 5 seconds with tap water and again thoroughly kneaded in a Petri dish per hand with 10 ml of a nutrient medium for one minute (post value).

1.0 ml and 0.1 ml of the non-diluted liquid of the nutrient media of the left and the right hand were streaked onto a total of 4 CSA plates. Within 30 minutes after the taking of samples the CSA plates were incubated for 24 h at 36° C. and the colonies counted.

The sum of the KBE of two successive dilutions is divided by the dilution factor and the obtained value then corresponds to KBE/ml non-diluted collection liquid:

[*n KBE* (of 1.0 ml)+*n KBE* (of 0.1 ml)]/1.1*10−1=number of *KBE*/ml non-diluted collection liquid.

The decade logarithm is taken of all bacterial counts per milliliter collection liquid. For calculating reasons the values of "0" (log 0=∞) must be set equal to "1" (log 1=0).

It turned out that the use of the antimicrobial composition in accordance with the invention results in a log 3 reduction according to DIN EN 1500.

Another standard method for the demonstration of an antimicrobial activity is anchored in DIN EN 13727 (draft December, 2009). DIN EN 13727 describes a test method aid the minimal requirements on the bactericide effect of chemical disinfectants and antiseptic products for determining whether an antiseptic has a bactericide effect or not in the scope of the working range described in the area of application. The products can only be tested in a concentration of 80% or below since the addition of the test germs and of the loading substance always causes a certain dilution. The test germs for a hygienic or surgical disinfection of hands are *Pseudomonas aeruginosa* (ATCC 15442), *Staphylococcus aureus* (ATCC 6538). *Enterococcus hirae* (ATCC 10541) and *Escherichia coli* K12 (NCTC 10538). The test temperature was 20° C., the exposure time for a hygienic disinfection of the hands is 60 seconds, for a surgical disinfection of the hands 5 minutes. Moreover, exposure times are checked according to the instructions of the manufacturer. Product test solutions are to be produced in at least three different concentrations in water with a standardized hardness, whereby one concentration must be in the effective range and one concentration in the non-effective range. The product in the delivery state may be used as one of the product test solutions; in this instance the highest tested concentration is 80 wt %. The number of cells in the test suspension is adjusted with the dilution agent to $1.5 \times 10^8$ KBE per ml to $5.0 \times 10^8$ KBE per ml. The loading substance must be selected according to the conditions of use set for the product. It must be sterile and produced with a ten times higher concentration than is required for the testing. In the case of a low load bovine serum albumin solution is used in a low concentration. In the case of a high load a mixture of bovine serum albumin solution in high concentration with sheep erythrocytes is used. For control, instead of a test suspension a validation suspension is used in which the test suspension is diluted with the dilution agent in such a manner that $3.0 \times 10^2$ KBE per ml to $1.6 \times 10^3$ KBE per ml result.

1.0 ml load substance and 1.0 ml test suspension are pipetted into a test tube. The stopwatch is immediately started, the mixture thoroughly mixed and the test tube placed for 2 min +/−10 s into a water bath adjusted to 20° C. After the passage of this time 8.0 ml of one of the product test solutions is added. The stopwatch is again started at the beginning of the addition, the mixture thoroughly mixed and the test tube placed for the selected exposure time t into a water bath adjusted to 20° C.

Immediately before the end of t the solution is again thoroughly mixed. After the passage of t a 1.0 specimen of the test mixture is transferred info a small tube with 8.0 ml neutralization medium and 1.0 ml wafer. The mixture is thoroughly mixed and placed in a water bath adjusted to 20° C. After a neutralization time (10+/−1) s (seconds) the mixture is thoroughly mixed and immediately a sample of 1.0 ml of the neutralized test mixture (containing neutralization medium, product test solution, loading substance and test suspension) is taken as double determination and seeded in the cast plate- or surface method.

In addition, 0.5 ml of this mixture is transferred into a small tube containing 4.5 ml of the neutralization medium in order to obtain the neutralized test mixture in a dilution of 10-1. Specimens of 1.0 ml were taken as a double determination from each small dilution tube and seeded in the surface method. When using the surface method each 1.0 ml specimen, that is divided into portions of approximately the same size, is spread onto a suitable number (at least two) of plates with TSA that are dry on the surface.

The exposure times were 15, 30 and 60 seconds at a product concentration of 40 wt %. The plates are incubated 24 h and counted in order to determine the number of colony-forming units (KBE). Upon an examination under simulated conditions of low load (0.3 g/l bovine serum albumin solution) or under conditions of high load (3 g/l bovine serum albumin solution and 3 g/l washed sheep erythrocytes; a product for hand disinfection must demonstrate a reduction of at least live decade-logarithmic stages (log 5).

It turned out that the use of the antimicrobial composition of the invention leads to a log 5 reduction in accordance with DIN EN 13727.

Furthermore, the method for the production of the antimicrobial compositions in accordance with the invention is essential for the invention. The person skilled in the art knows that tats and oils in alcohols can partially have a good solubility and that oil-in-water emulsions in which there is a high alcohol component in the aqueous phase are difficult to stabilise. The instability is shown, for example, by a complete solution of the oily phase in the alcoholic-aqueous phase. Given this background, the problem of producing a hydroalcoholic emulsion that is stable in storage and in which the alcoholic-aqueous phase has the properties of a gel noses a particular challenge.

Therefore, the invention also has as subject matter a method for the production of the previously described antimicrobial composition in accordance with the invention. The method preferably comprises the following steps that are carried out successively:

1. A mixture M1 consisting of
   a1) 8-15 wt % ethanol, 1-propanol, 2-propanol or their mixtures,
   c) 0.1-0.3 wt % of at least one thickener and
   e1) 4-18 wt % water
   is charged with a mixture M2 consisting of
   a2) 70-80 wt % ethanol, 1-propanol, 2-propanol or their mixtures,
   j) co-thickeners and
   d1) at least of one oil component soluble in the mixture consisting of a2 and j), and is agitated until the formation of a gel,
2. In a mixture consisting of
   e2) 0-14 wt % water, whereby e1) and e2) are supplemented to 4-18 wt % water, and
   b) 0.11-4.0 wt % of a silicone-containing emulsifier d2) at least one insoluble oil component is emulsified under agitation, whereby the oil components d1) and d2) are selected from unsaturated or saturated, linear or branched aliphatic hydrocarbons, fatty alcohols, fatty acid esters and their mixtures.
3. The emulsion (mixture M3) formed in step 2 is brought into the get phase and worked under slow agitation to a homogenous preparation.

A stable emulsion is obtained by the method that has a sufficient long-time stability in spite of the high amount of alcohol. Thus, in the previously described method at first a gel is produced and the working in of the oil phase subsequently follows in order to produce a hydroalcoholic emulsion. According to the invention the antimicrobial agent can be produced by an alternative method. In this alternative method the following steps are passed through:

1. A mixture M4 consisting of
   a1) 8-15 wt % ethanol, 1-propanol, 2-propanol or their mixtures,
   c) (0.1-0.3 wt % of at least one thickener and
   e1) 4-18 wt % water is charged with a mixture M5 consisting of
   b) 0.1-4.0 wt % of a silicone-con raining emulsifier and
   d1) 0.5-6.0 wt % of a mixture consisting of at least 3 oil components.
2. The mixture is agitated until an emulsion forms.
3. The emulsion formed is compounded with a mixture M6 consisting of
   a2) 70-80 wt % ethanol, 1-propanol, 2-propanol or their mixtures, j) co-thickeners and
   d2) at least one oil component soluble in the mixture consisting of a2 and j), whereby the oil components d1) and d2) are selected from unsaturated or saturated, linear or branched aliphatic hydrocarbons, fatty alcohols, fatty acid esters and their mixtures.
4. After the addition of the mixture M6 the composition is emulsified bather under agitation and agitated further at a low agitation speed.

Thus, in this method at first an emulsion is prepared into which the soluble oil components and the neutralization agent are subsequently worked in. Thus, the thickening of the preparation takes place at the end of the method for the production of a hydroalcoholic emulsion.

In the method in accordance with the invention the thickeners, oil components, silicone-containing emulsifiers and neutralization agents are used that are also used for the antimicrobial composition in accordance with the invention. They are also used in the preferred amounts used in the antimicrobial composition.

The invention is explained using the following example.

EXAMPLE 1

Production of an Antimicrobial Composition in Accordance with the Invention

| Raw material. | INCI designation | Amount [wt %] |
|---|---|---|
| Aqua purificata | Purified water | 10.16 |
| Ethanol 99%, 2-butanone denatured | Ethanol | 6 |
| Tegosoft ® liquid | Cetarylethylhexanoate | 0.25 |
| Tegosoft ® P | Isopropylpalmitate | 0.25 |
| Arlamol ® HD | Heptamethylnonane | 0.25 |
| Paraffinum subliquidum | Viscous paraffin | 1.8 |
| Abil ® Care XL 80 | Bis-PEG/PPG-20/5 PEG/PPG-20/5 dimethicone; methoxy PEG/PPG-25/4 dimethicone; capryl-/caprin-triglyceride | 0.5 |
| Carbopol ® ETD 2020 NF | Acrylate C10-30 alkyl acrylate cross polymer | 0.2 |
| Ethanol 99%, 2-butanone denatured | Ethanol | 80 |
| Lorol ® C$_{14}$/Nacol ® 14-95 | Myristyl alcohol or tetradecanol | 0.19 |
| Neutrol ® TE | Tetrahydroxypropyl-ethylene diamine | 0.4 |
| | | 100.0 |

60.0 g ethanol with the water were placed in a 2 liter beaker. The thickener was weighed into a second beaker and then the oils cetarylethylhexanoate, isopropylpalmitate, heptamethylnonane and Paraffinum subliquidum as well as the silicone-containing emulsifier were added. The components were agitated with each other. This oil phase was emulsified under agitation with an anchor agitator at an agitator speed of 250-800 rpm into the ethanolic aqueous phase. In order to form an emulsion the mixture was agitated approximately another 30 minutes at an agitator speed of 250-800 rpm.

The co-thickener Neutrol® TE and the oil component Lorol® C 14 were dissolved in the remaining ethanol and added to the emulsion under further agitation at an agitator speed of 400-800 rpm. The preparation was agitated until a homogeneous, agglomerate-free emulsion had been produced.

7ygb The antimicrobial composition obtained had a pH in the range of 8-9. The viscosity after 48 hours storage at room temperature was 2600-3800 mPa*s at 20° C. The viscosity was measured with a Brookfield rotation viscosimeter (spindle 2). For the determination the preparation was placed in a 600 ml beaker, tempered in a water bath at 20° C. (+/−0.5° C.) and 20 measurements at an interval of 15 seconds each at 10 rpm were made. The measured values were averaged in conclusion.

EXAMPLE 2

Production of Another Composition in Accordance with the Invention

| Raw material | INCI designation | Amount [wt %] |
|---|---|---|
| Aqua purificata | Purified water | 10.542 |
| Ethanol 99%, 2-butanone denatured | Ethanol | 5.858 |
| Arlamol ® HD | Heptamethylnonane | 0.500 |
| Paraffinum subliquidum | Viscous paraffin | 1.500 |
| Abil ® Care XL 80 | Bis-PEG/PPG-20/5 PEG/PPG-20/5 dimethicone; methoxy PEG/PPG-25/4 dimethicone; capryl-/caprin-triglyceride | 1.000 |
| Carbopol ® ETD 2020 NF | Acrylate C10-30 alkyl acrylate cross polymer | 0.200 |
| Ethanol 99%, 2-butanone denatured | Ethanol | 80.000 |
| Neutrol ® TE | Tetrahydroxypropyl-ethylene diamine | 0.400 |
|  |  | 100.000 |

The antimicrobial composition in accordance with example 2 was produced analogously to example 1.

Example 2 is a recipe with fewer oil components and less total oil content than example 1.

EXAMPLE 3

Production of Another Composition in Accordance with the Invention

| Raw material | INCI designation | Amount [wt %] |
|---|---|---|
| Aqua purificata | Purified water | 7.542 |
| Ethanol 99%, 2-butanone denatured | Ethanol | 5.858 |
| Tegosoft ® P | Isopropylpalmitate | 0.500 |
| Arlamol ® HD | Heptamethylnonane | 0.500 |
| Paraffinum subliquidum | Viscous paraffin | 3.000 |
| Abil ® Care XL 80 | Bis-PEG/PPG-20/5 PEG/PPG-20/5 dimethicone; methoxy PEG/PPG-25/4 dimethicone; capryl-/caprin-triglyceride | 1.000 |
| Carbopol ® ETD 2020 NF | Acrylate C10-30 alkyl acrylate cross polymer | 0.200 |
| Ethanol 99%, 2-butanone denatured | Ethanol | 80.000 |
| Lorol ® $C_{14}$/ Nacol ® 14-95 | myristyl alcohol or tetradecanol | 1.000 |
| Neutrol ® TE | Tetrahydroxypropyl-ethylene diamine | 0.400 |
|  |  | 100.000 |

The antimicrobial composition according to example 3 was produced analogously to example 1.

The invention claimed is:

1. An antimicrobial composition consisting of
   a) 80-95 wt % ethanol, 1-propanol, 2-propanol or their mixtures,
   b) 0.1-4.0 wt % of one or more silicone-containing emulsifiers containing both a lipophilic component and a hydrophilic component, wherein the silicone-containing emulsifiers are selected from the group consisting of cetyl PEG/PPG-10/1-dimethicone, bis-PEG/PPG-20/5 PEG/PPG-20/5-dimethicone, methoxy PEG/PPG-25/4-dimethicone, and mixtures thereof,
   c) 0.01-0.5 wt % of one or more thickeners based on cross-linked polyacrylic acid and its derivatives,
   d) 1.5-6.0 wt % of at least two oil components selected from the group consisting of skincare hydrocarbons, fatty alcohols, fatty acid esters and their mixtures, wherein the oil components are selected from the groups having i) rapid spread behavior, ii) average spread behavior and iii) slow spread behavior, whereby at least two oil components are selected from different groups i)-iii),
   e) 4-18 wt % water,
   f) 0.01-1.0 wt % co-thickener N,N,N',N'-tetrakis-(hydroxyalkyl)-ethylene diamine,
   g) 0-5.0 wt % of at least one of a diol or phenoxyethanol,
   h) 0-1.0 wt % pH regulators, selected from citric acid, lactic acid, tartaric acid, pyroglutamic acid, ascorbic acid, potassium hydroxide and/or sodium hydroxide, and
   i) 0-5 wt % opacifier, selected from insoluble substances that result in a whitish-opaque appearance.

2. The antimicrobial composition according to claim 1, wherein the amount of a) is 83-89 wt %.

3. The antimicrobial composition according to claim 1, wherein d) is at least three oil components.

4. The antimicrobial composition according to claim 1, characterized in that the antimicrobial composition is present as an emulsion, lotion, gel or hydrodispersion gel.

5. The antimicrobial composition according to claim 1, characterized in that by using the antimicrobial composition within 15 seconds a log 3 reduction according to DIN EN 1500 or a log 5 reduction according to DIN EN 13727 is achieved.

6. The antimicrobial composition according to claim 1, characterized in that the antimicrobial composition has a dynamic viscosity of 1 to 12 Pa*s, at 20° C. (+/−0.5° C.), measured with a Brookfield rotation viscosimeter model DV-II+, spindle sizes 2, 3, 4 or 5 at 10 rpm.

7. The antimicrobial composition according to claim 1, characterized in that the antimicrobial composition has an opacity value, measured as 90° scatter light value, of at least 200 NTU.

8. The antimicrobial composition according to claim 1, which is a disinfectant for animated surfaces containing microorganisms.

9. A method for disinfection of animated surfaces containing microorganisms, comprising applying to an animated surface the antimicrobial composition according to claim 1.

10. A method for the production of an antimicrobial composition, characterized in that a mixture M1 consisting of
   a1) 8-15 wt % ethanol, 1-propanol, 2-propanol or their mixtures,
   c) 0.1-0.3 wt % of at least one thickener and
   e1) 4-18 wt % water
   is charged with a mixture M2 consisting of
   a2) 70-80 wt % ethanol, 1-propanol, 2-propanol or their mixtures,
   j) co-thickeners and
   d1) at least one oil component soluble in the mixture consisting of a2 and j),
   and is agitated until the formation of a gel, and that a mixture M3 is introduced into the gel and processed to a homogeneous preparation, wherein mixture M3 consists of e2) 0-14 wt % water, whereby e1) and e2) are supplemented to 4-18 wt % water, and b) 0.1-4.0 wt % of a silicone-containing emulsifier containing both a lipophilic component and a hydrophilic component, and wherein the silicone-containing emulsifiers are selected from the group consisting of cetyl PEG/PPG-10/1-dimethicone, bis-PEG/PPG-20/5 PEG/PPG-20/5-dimethicone, methoxy PEG/PPG-25/4-dimethicone, and mixtures thereof, and d2) at least one insoluble oil component emulsified in it under agitation, whereby the oil components d1) and d2) are selected from unsaturated or saturated, linear or branched aliphatic hydrocarbons, fatty alcohols, fatty acid esters and their mixtures.

11. A method for the production of an antimicrobial composition, characterized in that a mixture M4 consisting of a1) 8-15 wt % ethanol, 1-propanol, 2-propanol or their mixtures, c) 0.1-0.3 wt % of at least one thickener and e1) 4-18 wt % water is charged with a mixture M5 consisting of b) 0.1-4.0 wt % of a silicone-containing emulsifier containing both a lipophilic component and a hydrophilic component, and wherein the silicone-containing emulsifiers are selected from the group consisting of cetyl PEG/PPG-10/1-dimethicone, bis-PEG/PPG-20/5 PEG/PPG-20/5-dimethicone, methoxy PEG/PPG-25/4-dimethicone, and mixtures thereof, and d1) 0.5-6.0 wt % of a mixture of at least 3 oil components, and agitated until an emulsion forms that is compounded with a mixture M6 consisting of a2) 70-80 wt % ethanol, 1-propanol, 2-propanol or their mixtures, j) co-thickeners and at least one oil component soluble in the mixture consisting of a2 and j), and is stirred further under agitation until homogeneity, whereby the oil components d1) and d2) are selected from unsaturated or saturated, linear or branched aliphatic hydrocarbons, fatty alcohols, fatty acid esters and their mixtures.

* * * * *